United States Patent
Sliski et al.

(10) Patent No.: US 6,301,328 B1
(45) Date of Patent: Oct. 9, 2001

(54) APPARATUS FOR LOCAL RADIATION THERAPY

(75) Inventors: Alan P. Sliski, Lincoln; Kenneth J. Harte, Carlisle, both of MA (US)

(73) Assignee: Photoelectron Corporation, Lexington, MA (US)

( * ) Notice: Subject to any disclaimer, the term of this patent is extended or adjusted under 35 U.S.C. 154(b) by 0 days.

(21) Appl. No.: 09/502,273

(22) Filed: Feb. 11, 2000

(51) Int. Cl.$^7$ ...................................................... A61N 5/10
(52) U.S. Cl. ................................................ 378/65; 378/64
(58) Field of Search ........................... 378/65, 64, 147, 378/148, 149

(56) References Cited

U.S. PATENT DOCUMENTS

| | | |
|---|---|---|
| 3,752,990 | 8/1973 | Fischer . |
| 4,646,338 | 2/1987 | Skillicorn . |
| 4,694,480 | 9/1987 | Skillicorn . |
| 5,090,043 | 2/1992 | Parker et al. . |
| 5,153,900 | 10/1992 | Nomikos et al. . |
| 5,165,093 | 11/1992 | Miller et al. . |
| 5,422,926 * | 6/1995 | Smith et al. .......................... 378/121 |
| 5,566,221 * | 10/1996 | Smith et al. .......................... 378/145 |
| 5,621,780 | 4/1997 | Smith et al. . |
| 5,748,699 | 5/1998 | Smith . |

* cited by examiner

Primary Examiner—David P. Porta
Assistant Examiner—Jurie Yun
(74) Attorney, Agent, or Firm—McDermott, Will & Emery

(57) ABSTRACT

A radiation applicator system is structured to be mounted to a radiation source for producing a beam of radiation for treating a localized volume of tissue, such as growing blood vessels in the eye that can cause macular degeneration. The applicator system includes an applicator and, in some embodiments, an adapter. The adapter is formed for fixedly securing the applicator to a radiation source, such as a radiosurgery system which produces a predefined radiation dose profile with respect to a predefined location along the radiation producing probe. The applicator includes a shank and an applicator head. A proximate end of the applicator shank couples to the adapter. A distal end of the shank includes the applicator head, which is adapted to produce a beam of radiation. The applicator head includes a radiation shield and a beam collimator. The radiation shield selectively blocks the emitted radiation so that the applicator can be held by a surgeon during treatment. The beam collimator extends from an aperture in the shield that forms and directs a beam of radiation at a target area. Applicator systems that form different size and shape beams of radiation can be provided to accommodate a wide range of treatment volumes and for use in different treatments.

17 Claims, 5 Drawing Sheets

APPARATUS FOR LOCAL RADIATION THERAPY

CROSS-REFERENCE TO RELATED APPLICATIONS

Not Applicable

STATEMENT REGARDING FEDERALLY SPONSORED RESEARCH

Not Applicable

REFERENCE TO MICROFICHE APPENDIX

Not Applicable

BACKGROUND OF THE INVENTION

This invention relates to a miniaturized, programmable radiation source for use in delivering substantially constant or intermittent levels of x-rays to a specified region and, more particularly, to an apparatus for delivering a controlled dose of radiation to a localized volume of tissue, such as a volume of tissue of the human body.

In the field of medicine, radiation is used for diagnostic, therapeutic and palliative treatment of patients. The conventional medical radiation sources used for these treatments include large fixed position machines such as linear accelerators ("LINACs"), smaller transportable radiation delivery machines such as high-dose-rate after loaders, and catheters for low-dose-rate brachytherapy. The current state of the art treatment systems utilize computers to generate complex treatment plans that require verification to insure proper treatment.

Typically, these systems apply doses of radiation in order to inhibit the growth of new tissue because it is known that radiation affects dividing cells more than the mature cells found in non-growing tissue. Thus, the regrowth of cancerous tissue in the site of an excised tumor can be treated with radiation to prevent the recurrence of cancer. Alternatively, radiation can be applied to other areas of the body to inhibit tissue growth, for example the growth of new blood vessels inside the eye that can cause macular degeneration.

Conventional radiation treatment systems, such as the LINAC used for medical treatment, utilize a high power remote radiation source and direct a beam of radiation at a target volume, such as a tumor inside the body of a patient. This type of treatment is referred to as teletherapy because the radiation source is located a predefined distance, typically on the order of one meter, from the target. This treatment suffers from the disadvantage that tissue disposed between the radiation source and the target is exposed to radiation.

An alternative treatment system utilizing a point source of radiation is disclosed in U.S. Pat. No. 5,153,900 issued to Nomikos et al., owned by the assignee of the present application, which is hereby incorporated by reference. The system includes a miniaturized, insertable probe capable of producing low power radiation in predefined dose geometries or profiles disposed about a predetermined location. One advantage of this system is that the radiation is applied to treat a predefined tissue volume, without significantly affecting the tissue in adjacent volumes.

A typical use of the described radiation therapy system involves positioning the insertable probe into the tumor or the site where the tumor or a portion of the tumor was removed to treat the tissue adjacent the site with radiation.

In order to facilitate controlled treatment of the site, it is desirable to support the tissue portions to be treated at a predefined distance from the radiation source. Alternatively, where the treatment involves the treatment of surface tissue or the surface of an organ, it is desirable to control the shape of the surface as well as the shape of the radiation field applied to the surface.

The treatment can involve the application of radiation, either continuously or intermittently, over an extended period of time. Therefore, it is desirable that the insertable probe be adjustably supported in a compliant manner to accurately position the radiation source with respect to the treated site and accommodate normal minor movements of the patient, such as movements associated with breathing.

Accordingly, it is an object of the present invention to provide an improved system for delivering radiation to a localized region.

SUMMARY OF THE INVENTION

The present invention is directed to a radiation applicator system which is mountable to a radiation source in order to apply a beam of radiation to a surface of a body to treat a volume of tissue. The radiation applicator system includes an applicator and, preferably, an adaptor. When included, the adapter couples the applicator to a radiation source. The applicator includes an applicator shank and an applicator head. The adapter may take any of a variety of forms, and may, for example, be integral with the shank, the radiation source, or may include one or more separate components which couple the shank to the radiation source. The adapter may also be formed by some combination thereof. In the preferred form, the adapter is a separate component that engages the applicator shank at the shank's proximate end and thereby allows coupling of the applicator to the radiation source, when the adapter is coupled to the radiation source. At the opposite and distal end of the applicator shank is the applicator head, which is used for producing a beam of radiation. Preferably, the applicator enables the production of a collimated beam of radiation having a predefined cross sectional area. The preferred cross-sectional area can be either circular or polygonal in shape, although other shapes can be provided.

In one embodiment, the radiation source includes an elongated probe and is adapted for producing a predefined radiation dose profile about a predetermined location with respect to the probe. In the this embodiment, the applicator can include a radiation shield adapted to surround at least a portion of the probe and a beam forming element, preferably a beam collimator, coupled to the radiation shield. Preferably, the beam collimator extends from an aperture in the radiation shield and defines the shape of the beam. A distal end of the beam collimator is sealed by a thin sheet of a material forming a substantially radiation transparent window for the radiation to pass through while isolating the probe of the radiation source from the environment of the area to be treated. Preferably each of the applicator, the radiation shield, and the beam collimator are constructed from biocompatible materials.

The applicator system is mounted to the radiation source and encase the source's elongated probe to form a self-contained treatment assembly. During the surgical procedure, the treatment assembly, including the applicator system and the radiation source, can be supported by a carrier system. The carrier support system can be adapted to support the treatment assembly in a substantially weightless configuration in order to facilitate positioning by the physician during surgery and to accommodate substantially minor movements by the patient.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE PREFERRED EMBODIMENTS

Figure 1A:
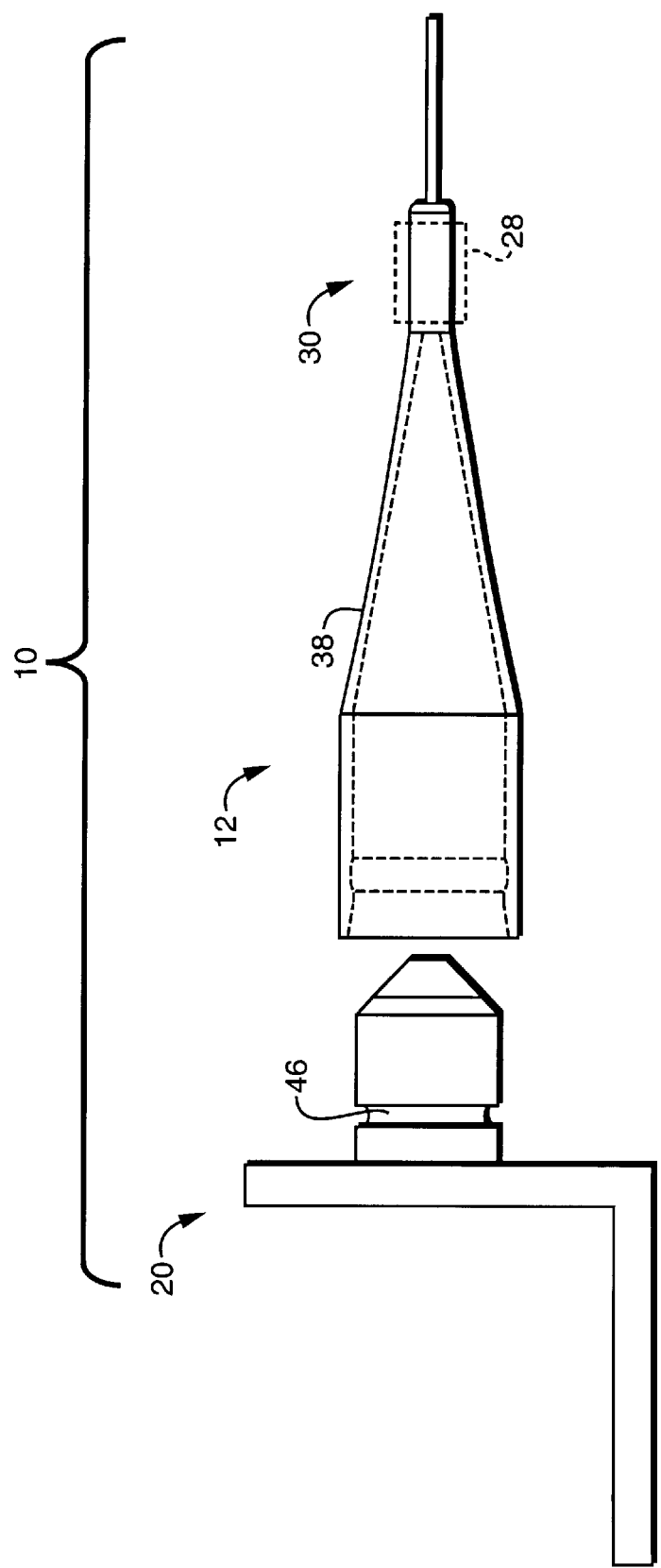
FIG. 1A is a diagrammatic exploded view of an applicator system, in accordance with the present invention.

FIG. 1A shows an applicator system 10 for applying a beam of radiation to a surface area of a volume of tissue to be treated. The applicator system 10 preferably includes an applicator 12 and an adapter 20, but in some embodiments an adapter may not be included. Applicator 12 includes a shank 38 and a head 30, wherein head 30 is located at a distal end of shank 38. In the preferred form, the adapter is a separate component, but in other embodiments the adapter may be integral with the shank or with the radiation source, or some combination thereof. A proximate end of shank 38 removably engages with adapter 20 to form the preferred applicator system 10. Adapter 20 is structured for attaching applicator system 10 to a radiation source (not shown). Applicator head 30 is adapted for producing a beam of radiation that can be applied to the surface area of a volume of tissue to be treated. The outer portion of the applicator head 30 can be fitted with grip 28 which can facilitate manipulation by a doctor during surgery.

Figure 1B:
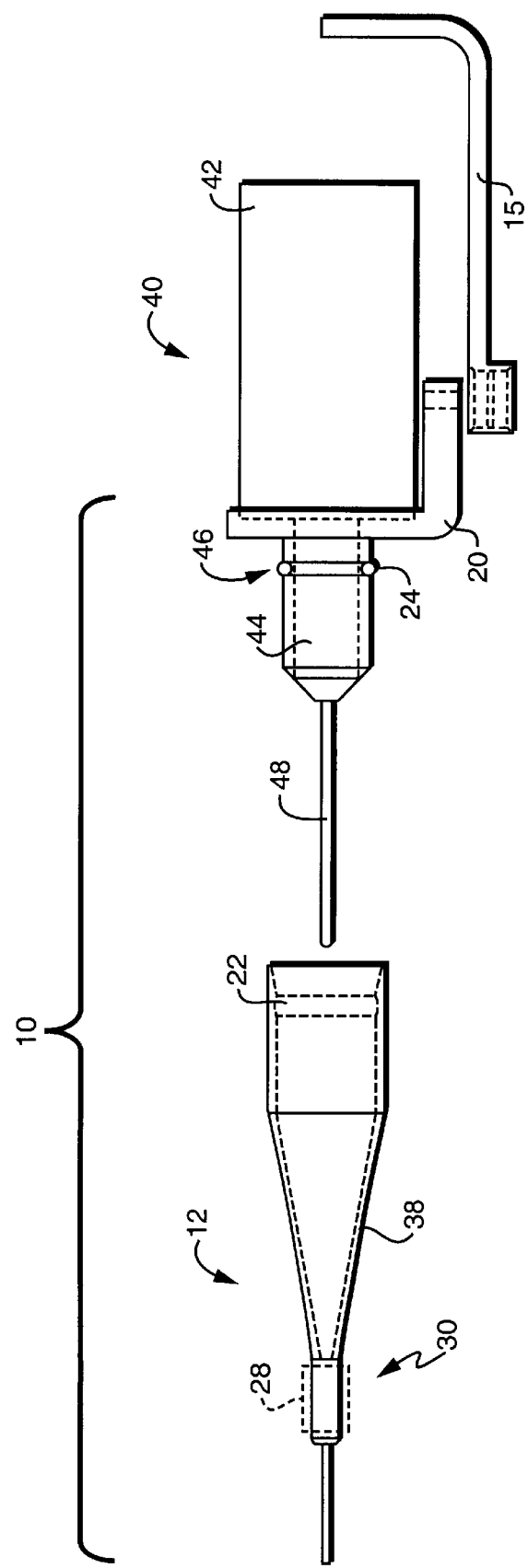
FIG. 1B is a diagrammatic exploded view of the applicator system of FIG. 1A and a prior art radiation source, with the applicator system adapter coupled to the radiation source.

FIG. 1B shows adapter 20 of applicator system 10 mounted on a radiation source, such as a radiosurgery system 40. The radiosurgery system 40 includes a housing 42, a barrel 44 and an elongated probe 48. The radiosurgery system 40 is adapted for generating a field of radiation having a predefined dose profile about the distal end of probe 48. The applicator system 10 is adapted to fit over probe 48 and barrel 44 of the radiosurgery system 40.

In the embodiment shown, adapter 20 is shown supported by a carrier support system arm 15, the carrier support system thereby supporting the radiosurgery system. The adapter includes a circumferential groove 46 and a retaining spring 24 (or O-ring) mounted in groove 46. A portion of spring 24 extends above the surface of the adapter 44 to facilitate engagement of applicator 12 to adapter 20. The proximate end of the applicator shank 38 is adapted to fit over adapter 20 and includes an interior, circumferential groove 22 which is adapted to receive the portion of the spring 24 that extends above the adapter groove 46.

Figure 2A:
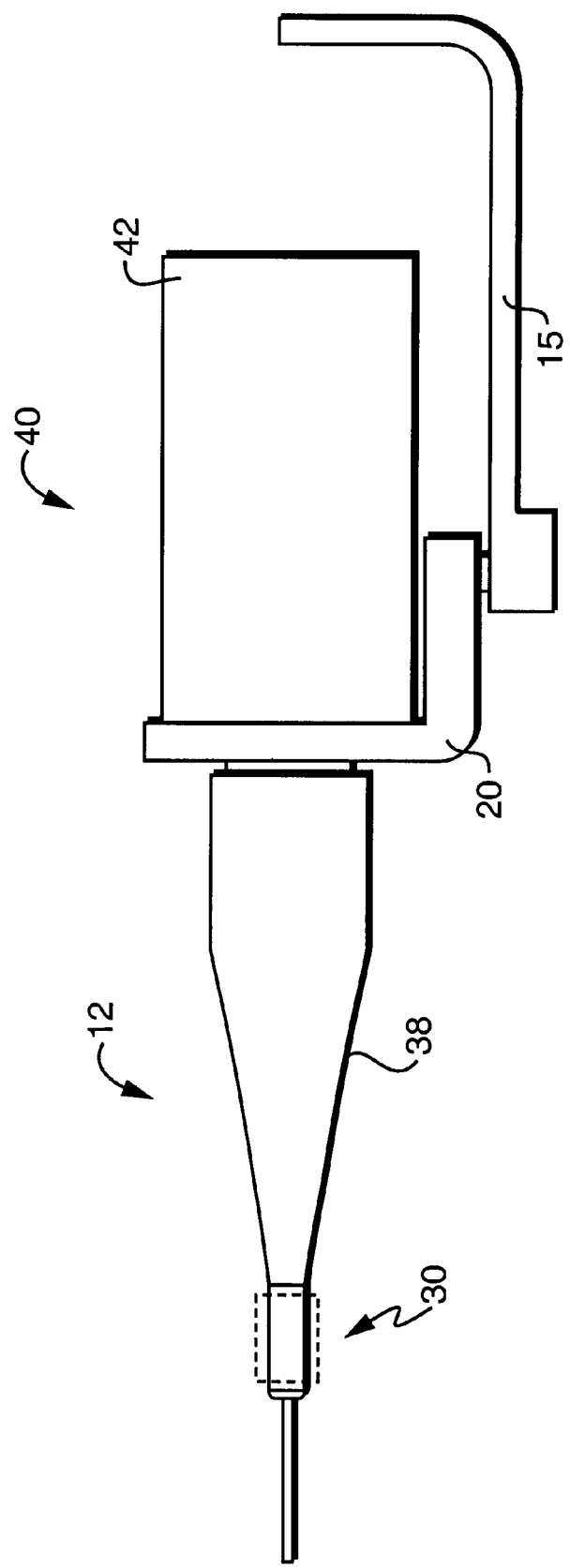
FIG. 2A is a diagrammatic view of the applicator system and radiation source of FIG. 1B in assembled form.
Figure 2B:
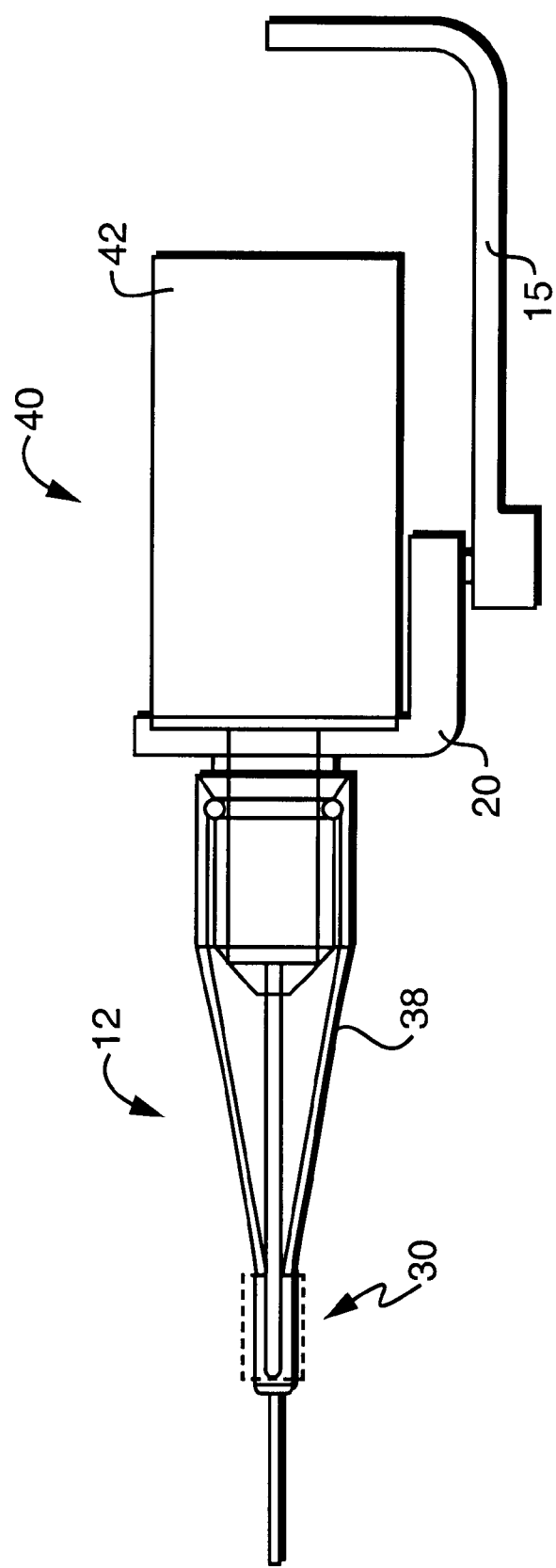
FIG. 2B is a diagrammatic assembled view showing a cross-section view of the applicator system and radiation source of FIG. 2A.

As shown in FIGS. 2A and 2B, the applicator 12 slidably fits over and couples to adapter 20, which is secured to radiosurgery system 40. When applicator 12 is slid on to adapter 20, spring 24 is compressed by the interior surface of shank 38 and, once groove 22 aligns with spring 24, the spring expands to fill groove 22, thereby securely coupling shank 38 of applicator 12 to adapter 20. Consequently, applicator 12 is secured over probe 48 of the radiosurgery system 40. As a person having ordinary skill will appreciate, other well known coupling methods and mechanisms can be used, for example: a bayonet coupling, a threaded coupling, spring loaded ball bearings and detents, and set screws.

Figure 3:
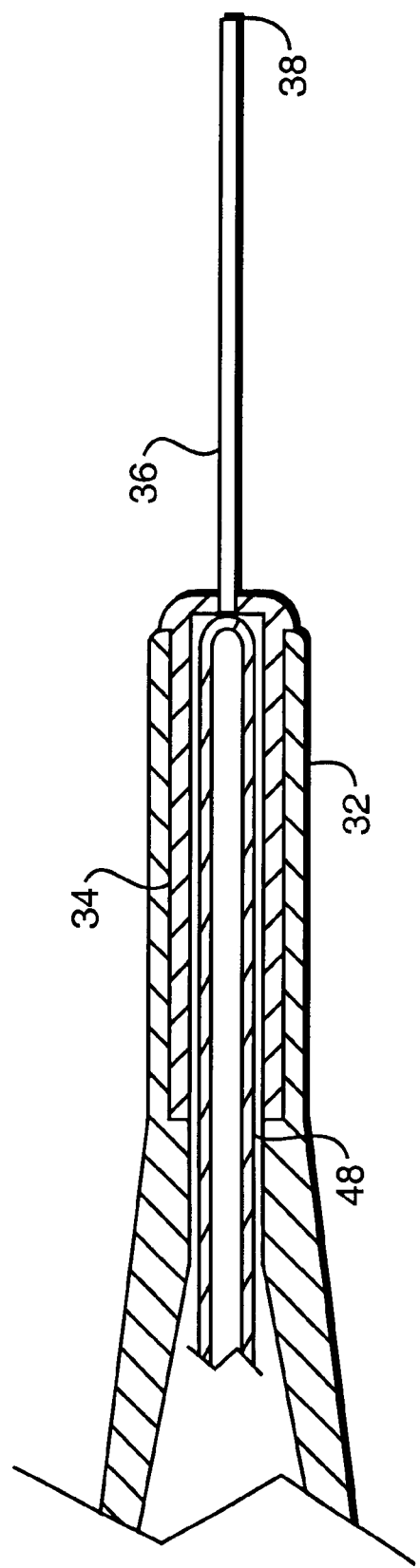
FIG. 3 is a diagrammatic view of the distal end of an applicator of FIG. 2B for forming and applying a beam of radiation to an area.

Applicator head 30 is adapted to receive the distal end of probe 48. As shown in FIG. 3, the applicator head 30 includes an applicator barrel 32 which, preferably, is sized to be held by the hand of a physician for use during surgery to apply a beam of radiation to an area of tissue to be treated. The applicator head 30 further includes a radiation shield 34, a beam forming element, such as beam collimator 36, and a beam window 38. Both the shield 34 and the beam collimator 36 are formed from a radiation absorbing material to block the radiation produced by the probe 48 from emanating from undesired portions of the applicator barrel 32. The beam collimator 36 extends from an opening in shield 34 and serves to provide a channel which forms and guides a beam of radiation from the probe 48 to the beam window 38. The beam of radiation passes through the beam window 38 and can be applied to an area of tissue to be treated.

Preferably, the radiation shield 34 and the beam collimator 36 are formed from a radiation absorbing material (i.e. a dense material having a high atomic number) that has sufficient strength, ductility and biocompatibility for the intended application. In the preferred embodiment for treatment of macular degeneration, the shield 34 is formed from a platinum—20% iridium alloy and the beam collimator 36 is formed from a 1 mm diameter round (or square) by 28 mm long tube of platinum—20% iridium alloy. The beam window 38 can be formed from any biocompatible material that is substantially transparent to the radiation produced at the end of the probe. Preferably, the beam window 38 is formed from a 0.5 micron thick biocompatible polymer material that is bonded to seal the distal end of the beam collimator 36. In the preferred embodiment, the beam window 38 is made of Ultem 1000, a polyetherimide by General Electric Company of Fairfield, Conn.

In the embodiment shown, the beam collimator 36 and the applicator 12 extend coaxially along the axis of the probe 48. As one of ordinary skill will appreciate, the beam collimator 36 can be coupled to the radiation shield 34 whereby the beam collimator 36 extends at an angle to the axis of the probe 48.

During treatment, the radiosurgery system 40 with the attached applicator system 10 may be supported by a gimbal mounted support system such as that disclosed in commonly owned U.S. patent application Ser. No. 09/502,473 (Attorney Docket No. PHLL-130), which is hereby incorporated by reference. Such an arrangement allows a physician applying treatment to guide the tip of the applicator without having to support the weight of the device for the duration of the treatment. An example of such a system is the carrier support system shown in part in FIGS. 1A, 2A, and 2B.

The above described system can be used to treat Macular Degeneration, a degenerative illness caused by the uncontrolled growth of new blood vessels resulting in loss of vision in the macula. The treatment involves inserting the beam collimator 36 though an opening in the cornea to apply radiation to the retina to inhibit the growth of the new blood vessels that could cause vision loss. The dosage of radiation (i.e. the energy level and duration) would be determined based upon the extent of the Macular Degeneration at the time of treatment.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A radiation applicator system for use with a radiation source for facilitating the application of a dose of radiation to a volume, said radiation applicator system comprising:
   A) an applicator, adapted to substantially encase a radiating probe of said radiation source, said applicator including:
      i) a shank having a proximate end and a distal end; and
      ii) a head secured to said shank distal end and capable of forming a collimated beam of radiation.

2. A radiation applicator system according to claim 1 wherein said collimated beam of radiation has a predefined cross-sectional shape.

3. A radiation applicator system according to claim 1 wherein said head is adapted for producing a beam of radiation having a substantially circular cross section.

4. A radiation applicator according to claim 1 wherein said head is adapted for producing a beam of radiation having a substantially polygonal cross section.

5. A radiation applicator system according to claim 1 wherein said radiation source probe is an elongated probe adapted for producing a predefined radiation dose profile about a predetermine location with respect to the probe; and
   said head includes a radiation shield adapted for surrounding at least a portion of said elongated probe and a beam forming element, coupled to said radiation shield, adapted for forming a beam of radiation.

6. A radiation applicator system according to claim 5 wherein said radiation shield includes a substantially tubular shield mounted in said radiation applicator and said beam forming element includes an elongated tube extending from said tubular shield.

7. A radiation applicator system according to claim 5 wherein said radiation shield includes a substantially tubular shield mounted in said radiation head and said beam forming element includes an elongated tube, formed of a radiation shielding material, having a proximal end coupled to said tubular shield and extending from said tubular shield to a distal end and said distal end includes a radiation transparent window sealing said distal end.

8. A radiation applicator system according to claim 7 wherein said radiation transparent window includes a thin sheet of a stainless steel material or titanium or biocompatible polymer.

9. A radiation applicator system according to claim 5 wherein the beam forming element is substantially comprised of an iridium alloy.

10. A radiation applicator system according to claim 1, further comprising:

B) an adapter, including:
      i) a first coupler suited for mated engagement with said shank proximate end; and
      ii) a second coupler suited for mated engagement with said radiation source.

11. A radiation applicator system for use with a radiation source for facilitating the application of a dose of radiation to a volume, said radiation applicator system comprising:
   A) an applicator, adapted to substantially encase a radiating probe of said radiation source, said applicator including:
      i) a shank having a proximate end and a distal end; and
      ii) a head secured to said shank distal end and capable of forming a collimated beam of radiation; and
   B) an adapter, including:
      i) a first coupler suited for mated engagement with said shank proximate end; and
      ii) a second coupler suited for mated engagement with said radiation source.

12. A radiation treatment system for applying a dose of radiation to a treatment area or volume, said radiation treatment system comprising:
   a radiation source including a housing and an elongated probe extending from said housing, said radiation source being adapted to produce a predefined radiation dose distribution with respect to a predefined location along said probe;
   a radiation treatment applicator system coupled to said radiation source and adapted to form a collimated beam of radiation and to apply said collimated beam of radiation to the treatment area.

13. A radiation treatment system according to claim 12, wherein said radiation treatment applicator system includes:
   A) an applicator, adapted to substantially encase a radiating probe of said radiation source, said applicator including:
      i) a shank having a proximate end and a distal end; and
      ii) a head secured to said shank distal end and capable of forming a collimated beam of radiation.

14. A radiation treatment system according to claim 13, wherein the applicator system further includes:
   B) an adapter, including:
      i) a first coupler suited for mated engagement with said shank proximate end; and
      ii) a second coupler suited for mated engagement with said radiation source.

15. A radiation treatment system according to claim 12 wherein said collimated beam of radiation has a predefined cross-sectional shape.

16. A radiation applicator according to claim 12 wherein said treatment applicator system includes a radiation shield adapted to surround at least a portion of said elongated probe and a beam forming element, coupled to said radiation shield, adapted to form a beam of radiation.

17. A radiation treatment system according to claim 16 wherein said radiation shield includes a substantially tubular shield mounted in said treatment applicator system and said beam forming element includes an elongated tube extending from said tubular shield.

* * * * *